United States Patent [19]
Drane et al.

[11] Patent Number: 5,215,083
[45] Date of Patent: Jun. 1, 1993

[54] APPARATUS AND METHOD FOR ARRHYTHMIA INDUCTION IN ARRHYTHMIA CONTROL SYSTEM

[75] Inventors: Geoffrey A. Drane, Annandale; Steven M. Weiss, West Pymble, both of Australia

[73] Assignee: Telectronics Pacing Systems, Inc., Englewood, Colo.

[21] Appl. No.: 773,048

[22] Filed: Oct. 7, 1991

[51] Int. Cl.⁵ ............................................. A61N 1/36
[52] U.S. Cl. ................................................ 128/419 D
[58] Field of Search ................................. 128/419 D

[56] References Cited

U.S. PATENT DOCUMENTS

| | | | |
|---|---|---|---|
| 4,114,628 | 9/1978 | Rizk | 120/419 D |
| 4,300,567 | 11/1981 | Kolenik et al. | 128/419 D |
| 4,375,817 | 3/1983 | Engle et al. | 128/419 D |
| 4,384,585 | 5/1983 | Zipes | 128/419 D |
| 4,548,209 | 10/1985 | Wielders et al. | 128/419 D |
| 4,850,357 | 7/1989 | Bach, Jr. | 128/419 D |
| 5,044,367 | 9/1991 | Endres et al. | 128/419 D |
| 5,074,301 | 12/1991 | Gill | 128/419 D |
| 5,083,562 | 1/1992 | de Coriolis et al. | 128/419 D |
| 5,105,809 | 4/1992 | Bach, Jr. et al. | 128/419 D |

FOREIGN PATENT DOCUMENTS 0310216 3/1989 European Pat. Off. .
0473002 3/1992 European Pat. Off. .
WO9211064 7/1992 PCT Int'l Appl. .

Primary Examiner—Lee S. Cohen
Assistant Examiner—Jeffrey R. Jastrzab
Attorney, Agent, or Firm—Gottlieb, Rackman & Reisman

[57] ABSTRACT

An implantable medical device and method for providing therapy to a patient's inadequately functioning heart are disclosed. The device and method utilize a defibrillation electrode lead system to deliver defibrillation therapy to the patient's heart, and a defibrillator to provide the defibrillation therapy that is delivered by the defibrillation electrode lead system. The defibrillator includes a charge storing circuit for storing an electrical charge therein. Controls are employed for charging the charge storing circuit to an appropriately high energy level for use in defibrillation therapy, in response to a detected tachycardia condition, and for charging the charge storing circuit to an appropriately low energy level for selectively inducing an arrhythmia in the patient's heart. Switching circuitry is utilized to couple the charge storing circuit to the defibrillation electrode lead system; and, controls are provided for selectively actuating the switching circuitry to generate a plurality of micro-shocks from the low energy electrical charge in the charge storing circuit and to deliver the micro-shocks to the defibrillation electrode lead system.

37 Claims, 7 Drawing Sheets

APPARATUS AND METHOD FOR ARRHYTHMIA INDUCTION IN ARRHYTHMIA CONTROL SYSTEM

TECHNICAL FIELD

This invention relates to implantable medical devices which automatically and therapeutically monitor the cardiac condition of a patient by sensing the patient's intrinsic cardiac rhythm, particularly for the presence of tachyarrhythmias, and which deliver therapy in the form of electrical energy to cardiac tissue in an attempt to revert such tachyarrhythmias and restore the heart to a normal sinus rhythm. In particular it relates to an apparatus and method for the induction of arrhythmias such as ventricular fibrillation in an implantable medical device which is capable of delivering defibrillation therapy to a patient's inadequately functioning heart. Preferably, the implantable defibrillator also has the capability of delivering bradycardia and antitachycardia pacing therapies when necessary.

PRIOR ART

U.S. Pat. No. 3,857,398 to Rubin describes a combined pacer/defibrillator. This device either performs a bradycardia pacing or a defibrillation function depending on the detection of a VT/VF. If a VT/VF is detected, the device is switched to the defibrillating mode. After a period of time to charge the capacitor, a defibrillation shock is delivered to the patient. This device has no provision for antitachycardia pacing and is unable to provide fibrillation induction either through the pacing circuitry or the defibrillation circuitry.

A multiprogrammable, telemetric, implantable defibrillator is disclosed in Co-pending patent application Ser. No. 576,178 to N. L. Gilli et al., entitled "Reconfirmation Prior to Shock for Implantable Defibrillation," filed Aug. 29, 1990. The Gilli et al. device contains a bradycardia support system as well as a high energy shock system to revert ventricular tachycardias to normal sinus rhythm. On reconfirmation of the presence of a tachycardia, a shock is delivered to the patient at a predetermined time or when the desired energy level is reached. This implantable pacemaker/defibrillator does not include an antitachycardia pacing facility and therefore cannot be used to induce either ventricular tachycardias or ventricular fibrillations by delivering a rapid succession of pacing pulses through the pacing circuitry. Furthermore, there is no provision in the device for inducing a VT/VF by means of the defibrillation circuitry.

A further development in the field of combined implantable devices is described in U.S. Pat. No. 4,940,054 to R. Grevis et al., entitled "Apparatus and Method for Controlling Multiple Sensitivities in Arrhythmia Control Systems Including Post Therapy Pacing Delay." This device is a microcomputer based arrhythmia control system which is programmable by means of a telemetric link. The device provides single chamber bradycardia support pacing, antitachycardia pacing, and cardioversion or defibrillation shocks for restoring normal sinus rhythm to a patient. This implantable pacemaker/defibrillator device incorporates a facility to induce ventricular fibrillation and ventricular tachycardia. This is for the purpose of testing and evaluating the effectiveness of the programmed therapy.

The method of arrhythmia induction in the Grevis et al. device is performed by high rate pacing in accordance with preset or programmed timing regimes using the normal pacemaker pacing circuitry. This method is usually successful when it is desired to induce a VT. However, problems have arisen when attempting to induce VF, whereby the device has proven to be inadequate at times. The pacing circuitry in the Grevis et al. device includes a voltage pump circuit and a capacitor that is charged to the required amplitude for a pacing pulse. When the device is pacing at the bradycardia pacing rate or is required to induce a ventricular tachycardia, the output switch between the capacitor and the pacing electrodes is turned on and off at the pacing rate, providing sufficient time for the capacitor to acquire it's maximum charge each time a pacing pulse is generated.

However, when the Grevis et al. device is required to induce a VF, the extremely high pacing rate required (in the order of 50 pulses per second) places an excessive demand on the circuitry to charge the capacitor at this high switching rate. Hence, in a relatively short time a voltage droop occurs as there is not enough time between successive pacing pulses for the capacitor to be fully charged by the voltage pump circuit. This rapidly lowers the maximum attainable voltage for each pacing pulse generated. Accordingly, a non-capture situation arises and, therefore, a failure to achieve fibrillation induction.

Moreover, in devices such as the Grevis et al. device fibrillation induction is initiated using the pacing circuitry and the sense/pace lead system of the device. Therefore, due to the limited amplitudes of pacing pulses, which have maximum values typically in the range of 7-10 volts, capture may often be unattainable solely for the reason of insufficient pulse energy.

Additionally, it would not be possible to use such a system to induce fibrillation via the defibrillation lead system. The principal reason for this is due to the large surface area of a defibrillator lead, typically known in the art as a patch. This large patch surface area is generally about 2 or more orders of magnitude higher than the area of a pacing tip. As it is a sufficient level of current density at the electrode interface with the heart which achieves capture, and since current density is equal to current divided by surface area, then it would follow that in the case of a much greater surface area patch, a significantly higher current is correspondingly necessary. In view of the foregoing, such a level of current, two or more levels of magnitude greater than that generated through the pacing circuitry via the sense/pace lead system, can only be achieved using the defibrillation circuitry and the defibrillation lead system.

Thus, in certain patients where it has not been possible to successfully achieve an induced VF using the Grevis et al. device, the device has proved disadvantageous and not in the complete interests of patient safety, especially since the individually physician-programmed therapies related to the least time-consuming therapy mode and the most effective defibrillation energy generally have not been tested and evaluated at the time of implant or patient follow-up.

It is therefore an object of the present invention to provide an improved method and apparatus for effectively inducing VF's and other arrhythmias in a patient's heart.

It is another object of the invention to provide an improved implantable pacemaker/defibrillator device for effectively inducing VF's and other arrhythmias in a patient's heart to facilitate successful testing and evaluation of therapies and other operations of the implantable device when required by a patient's physician.

It is also an object of the invention to provide an improved implantable device capable of effectively inducing fibrillation and other arrhythmias, without the need to add extra hardware circuitry components on the device, by providing software instructions to the microprocessor thereof, which instructions control existing defibrillation hardware circuitry and thus save critical space in the device.

It is a further object of the invention to provide for improved induction of VF's and other arrhythmias by an implantable pacemaker/defibrillator device, utilizing the same circuitry of the device as that which provides the defibrillation shock therapy, whereby the electrical stimuli which induce the fibrillation may be delivered by means of the defibrillation electrode system.

It is another object of the invention to provide a device capable of inducing ventricular tachycardia and ventricular fibrillation and other arrhythmias in a patient's heart by means of electrical stimuli, delivered via defibrillation circuitry of the device, wherein the electrical stimuli take the form of micro-shocks delivered in rapid succession.

It is a still further object of the invention to include in an implantable arrhythmia control system means for controlling various timing aspects of the micro-shocks for the purpose of delivering the micro-shocks at an optimal interval and pulse width for induction of the desired arrhythmia.

It is yet another object of the invention to provide a method and apparatus capable of controlling the phase of individual micro-shock waveforms delivered during arrhythmia or fibrillation induction, thus allowing the delivery of different phases of micro-shock waveforms such as monophasic, biphasic, triphasic, and other multiphasic waveforms.

Further objects and advantages of the invention will become apparent as the following description proceeds.

SUMMARY OF THE INVENTION

Briefly stated, and in accordance with one embodiment of the invention, there is provided an implantable medical device for providing therapy to a patient's inadequately functioning heart. The device comprises: means for detecting fibrillation; a defibrillation electrode lead system for delivering defibrillation therapy to the patient's heart; defibrillation circuit means for providing defibrillation therapy to the defibrillation electrode lead system, the defibrillation circuit means including means for storing an electrical charge therein, first control means coupled to the charge storing means for charging the charge storing means to an appropriately high energy level for use in defibrillation therapy, in response to a detected tachycardia condition, and for charging the charge storing means to an appropriately low energy level for selectively inducing an arrhythmia in the patient's heart, and switching means for coupling the charge storing means to the defibrillation electrode lead system; the device further including second control means coupled to the switching means for selectively actuating the switching means to generate a plurality of micro-shocks from the low energy electrical charge in the charge storing means and to deliver the micro-shocks to the defibrillation electrode lead system for inducing the arrhythmia in the patient's heart.

In accordance with another aspect of the invention the implantable device preferably includes timing means which controls the intervals, pulse widths and duration of delivery of the micro-shocks. In this case the micro-shocks may be delivered continuously to the patient for a finite duration controlled by the timer or, in an alternative embodiment of the invention, the micro-shocks may be delivered in a series of one or more trains. The device may also include means for sensing the R-wave of the patient's heart for triggering the timing of the start of delivery of the series of trains.

In accordance with further aspects of the invention the device is preferably capable of synchronizing the delivery of at least a portion of a train of micro-shocks to a patient's T-waves; the length of the series of trains and the micro-shock pulse widths are preferably programmable parameters which may be programmed by the physician to suit a patient's individual needs; the device may include means for reversing the polarity of at least a portion of the micro-shocks delivered during fibrillation induction; and, each alternate individual micro-shock is preferably reversed in polarity from intermediate individual micro-shocks for the purpose of charge balancing.

BRIEF DESCRIPTION OF THE DRAWINGS

While the specification concludes with claims particularly pointing out and distinctly claiming the subject matter regarded as the invention herein, it is believed that the present invention will be more readily understood from the following detailed description, taken in conjunction with the accompanying drawings, in which:

DETAILED DESCRIPTION

As used herein, the following terms have the meanings shown:

"Tachyarrhythmia" refers to any fast abnormal rhythm of the heart which may be amenable to treatment by electrical discharges and specifically includes supraventricular tachycardia (SVT), ventricular tachycardia (VT), ventricular flutter and ventricular fibrillation (VF).

"Defibrillation" refers to the discharge of electrical energy into cardiac tissue in an attempt to terminate or revert a tachycardia and may range from a high (40 Joules or more) to a low (less than 1 Joule) of energy discharge. The discharge may be monophasic or biphasic but is not restricted to these waveforms. Defibrillation shocks may or may not be synchronized to the rhythm of the heart.

"Cardioversion" is defined as a particular example of defibrillation and generally refers in the pacemaker and defibrillation art to lower energy shocks in comparison to defibrillation. Cardioversion shock is usually synchronized to the patient's intrinsic R-wave at the time of a delivery.

"Micro-shock" is defined as a low level electrical stimulus, generally in the range of 5-15 volts, but in certain circumstances it may be as low as or less than 1 volt and as high as or more than 40 volts, and is delivered to the patient's heart through defibrillation or cardioversion circuitry. Micro-shocks are not delivered singly as is generally the case with higher energy cardioversion or defibrillation shocks which have the purpose of reverting a tachyarrhythmia in a patient's heart so as to restore normal sinus rhythm. In contrast they are delivered in rapid succession either continuously for a finite predetermined time interval, or in association with a train of micro-shocks, in order to induce the condition of fibrillation or other arrhythmia in a patient's heart that is beating at a normal sinus rhythm.

Figure 1A:
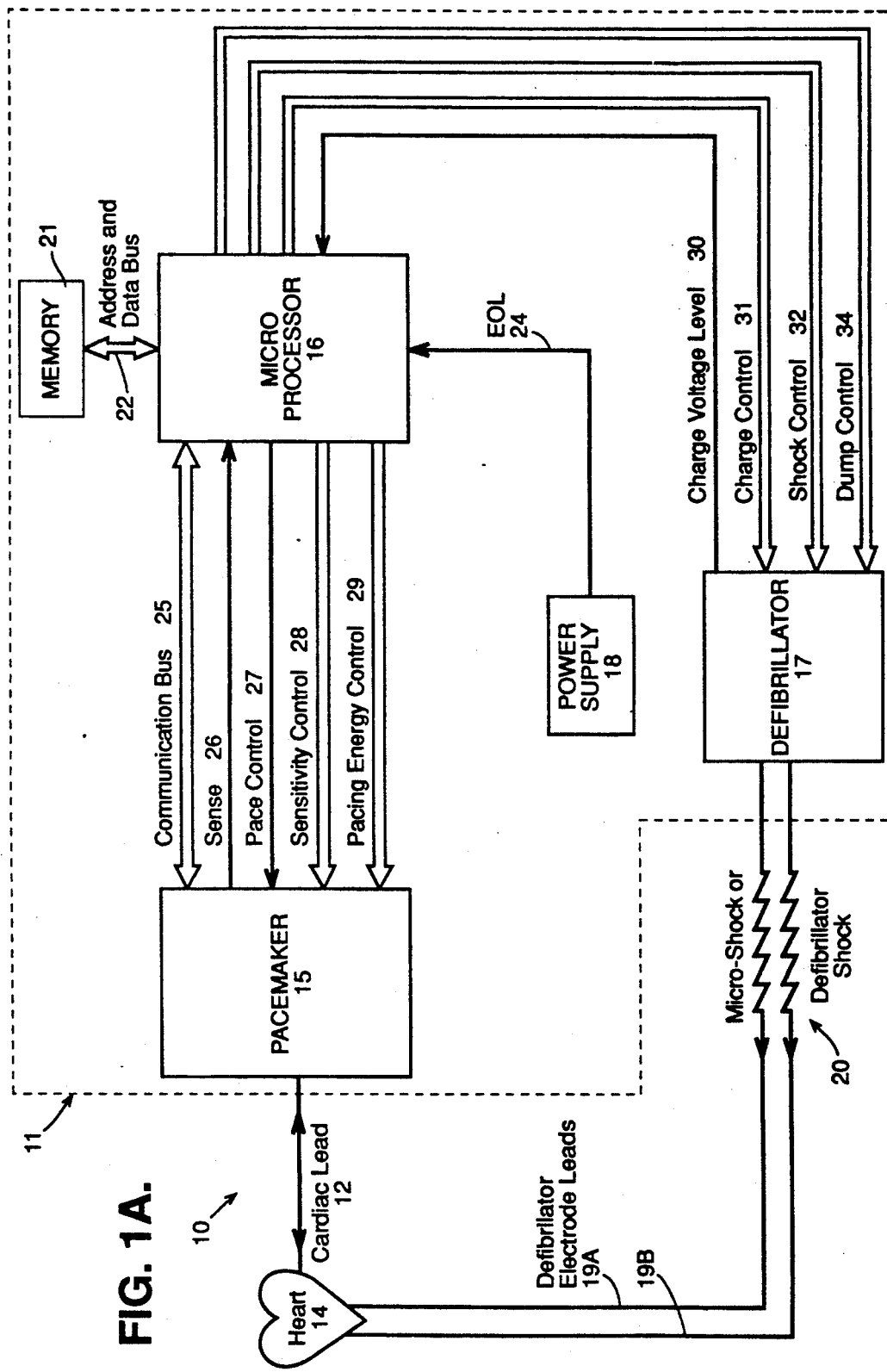
FIG. 1A depicts a block diagram of an arrhythmia control system in accordance with one embodiment of this invention.

Referring to FIG. 1A, there is depicted a block diagram of an arrhythmia control system, shown generally at 10. System 10 is designed to be implantable and includes a pulse module, shown generally at 11, and appropriate leads. More particularly, system 10 will generally include a cardiac lead system 12 extending to the atrium/ventricle of a patient's heart 14 for the administration of therapy to the atrium/ventricle. System 10 generally also includes a pacemaker 15 for the detection of analog signals representing cardiac electrical activity and for the delivery of pacing pulses to the heart; a microprocessor 16 which, in response to various inputs received from the pacemaker 15 as well as from a defibrillator 17, performs various operations so as to generate different control and data outputs to both pacemaker 15 and defibrillator 17; and a power supply 18 for the provision of a reliable voltage level to pacemaker 15, microprocessor 16 and defibrillator 17 by suitable electrical conductors (not shown). Defibrillator 17 produces a high voltage to charge its capacitors and then discharges them in response to control signals from microprocessor 16. Defibrillator electrode leads 19A and 19B transfer the energy of a defibrillator shock or a micro-shock 20 from the implanted pulse module to the surface of the heart 14. It is also possible to have one lead at one polarity while the defibrillator case is used as the opposite polarity. However, it may be possible to have several electrodes in the configuration.

Microprocessor 16 is connected to an external memory 21 by an address and data bus 22. An end-of-life (EOL) signal line 24 is used to provide, to microprocessor 16, a logic signal indicative of the approach of battery failure in power supply 18.

As more fully described below, microprocessor 16 and pacemaker 15 are connected by a communication bus 25, a sense line 26, a pace control line 27, a sensitivity control bus 28, and a pacing energy control bus 29. As also more fully described below, microprocessor 16 is connected to defibrillator 17 by a charge level line 30, a charge control bus 31, a shock control bus 32, and a dump control bus 34.

For the purposes of this invention, fibrillation or other arrhythmias can be induced to the ventricles of a patient's heart 14 by the delivery of a train of small defibrillator shocks (micro-shocks) from the defibrillator 17 to defibrillator electrode leads 19A and 19B. For this to take place, the defibrillator 17 is controlled by microprocessor 16 by charge control line 31 and shock control line 32. As more fully described below, microprocessor 16 delivers a signal to charge control line 31 which initiates charging of the capacitor in defibrillator 17. After a predetermined time (in the order of milli-seconds), the microprocessor 16 turns off the charge control signal 31 and turns on the shock control signal 32. After activating shock control switches 106, 107, 108, and 109 shown in FIG. 4 (to be described in greater detail hereinafter) for a pre-determined time (again in the order of milli-seconds) and in a pre-determined configuration of phases and electrodes, shock control signal 32 is turned off by the microprocessor 16. This sequence is repeated after a certain interval (typically in the order of milliseconds) as controlled by a timer within the microprocessor 16. Furthermore, each time the sequence is repeated, it may or may not be repeated in the same configuration. To obtain one mode of charge balancing, for example, different shock control switches may be activated on every alternate discharge thus reversing the polarity. For the purpose of arrhythmia or fibrillation induction, charged voltage level line 30 and charge control line 34 are not necessarily used.

Figure 1B:
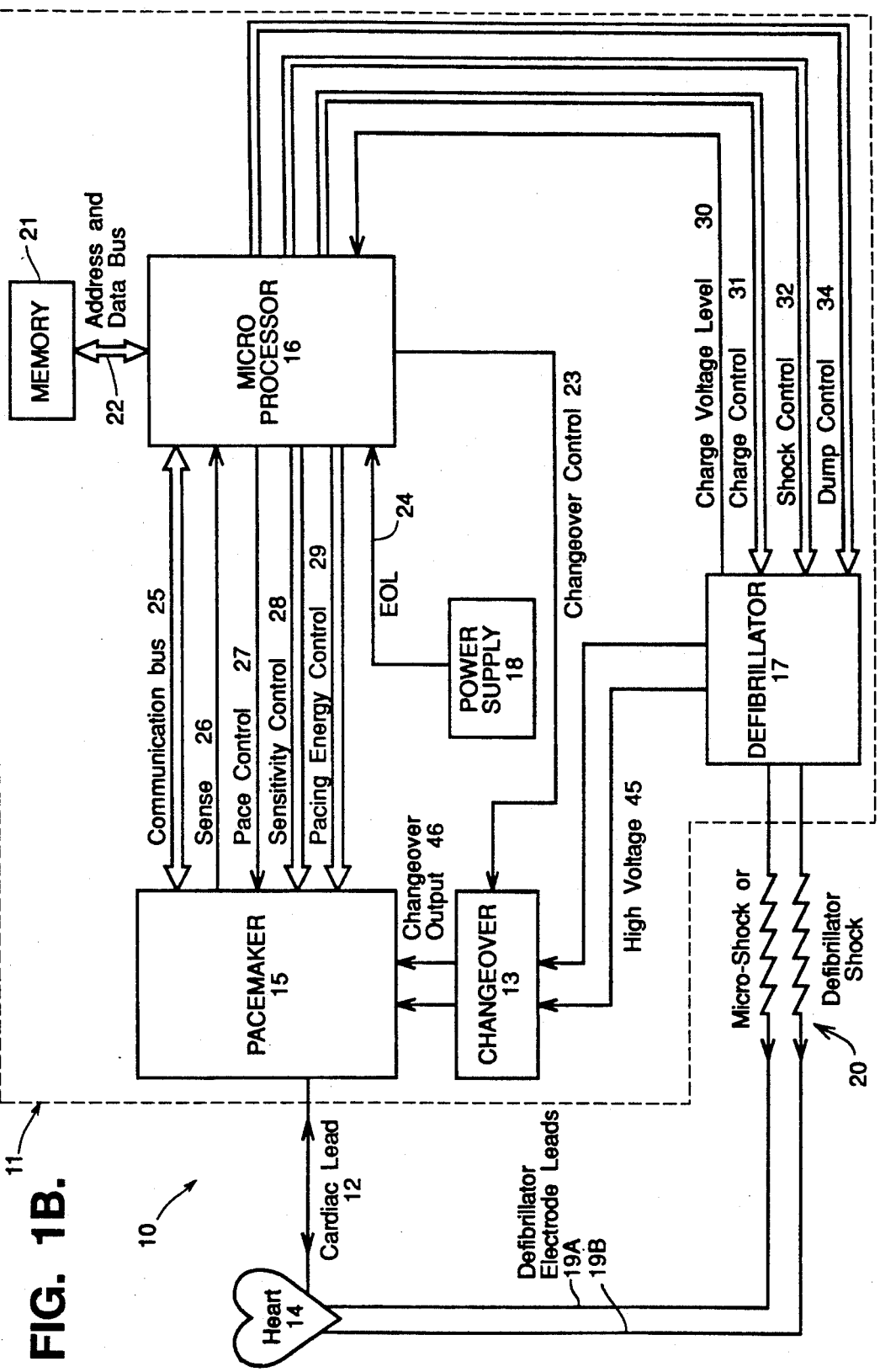
FIG. 1B depicts a block diagram of an arrhythmia control system in accordance with another embodiment of this invention.

Referring to FIG. 1B, there is shown an alternate embodiment of the pulse module 11 shown in FIG. 1A. In this embodiment, the energy from defibrillator 17 is delivered to the heart 14 via the pacemaker 15 and cardiac lead system 12. As shown, high voltage energy from defibrillator 17 is passed via a high voltage output line 45 to a changeover module 13 enroute to pacemaker 15. Module 13 is controlled by microprocessor 16 via a changeover control line 23. When a control signal is passed from microprocessor 16 along changeover control line 23 to the changeover module 13, appropriate circuitry within changeover 13 connects the voltage on high voltage output line 45 from defibrillator 17 to pacemaker 15 via a changeover output line 46. In this embodiment, pacemaker 15 incorporates additional circuitry to protect a pacing pulse generator circuit 36 shown in FIG. 2 (to be described in greater detail hereinafter) and a sensing QRS detector circuit 37A, also shown in FIG. 2, from possible damage from the voltages delivered along changeover output line 46. This protection circuitry may additionally be controlled by microprocessor 16 along pace control line 27.

By appropriate controls from microprocessor 16 along pacing control line 27, changeover control line 23 and shock control line 32, the proportion of energy delivered to each of cardiac lead system 12 and defibrillator electrode leads 19A and 19B (and ultimately to the heart 14) can be controlled for each micro-shock in the train and for each train of micro-shocks. Hence, for each micro-shock delivered to the heart 14, a portion of the micro-shock's energy can be delivered via the cardiac lead system 12 and the remainder delivered via defibrillator electrode leads 19A and 19B. Alternatively, some of the micro-shocks in a train of micro-shocks can be delivered via cardiac lead system 12 with the remainder of the micro-shocks being delivered via defibrillator electrode leads 19A and 19B. Similarly, a combination of a portion of the microshock's energy and a number of the micro-shocks could be delivered via cardiac lead system 12 with the remaining portion and number of micro-shocks being delivered via defibrillator electrode leads 19A and 19B. Also, the apportioning of energy delivered via cardiac lead system 12 and via defibrillator electrode leads 19A and 19B could be performed with respect to entire trains of micro-shocks in a series of trains.

Figure 2:
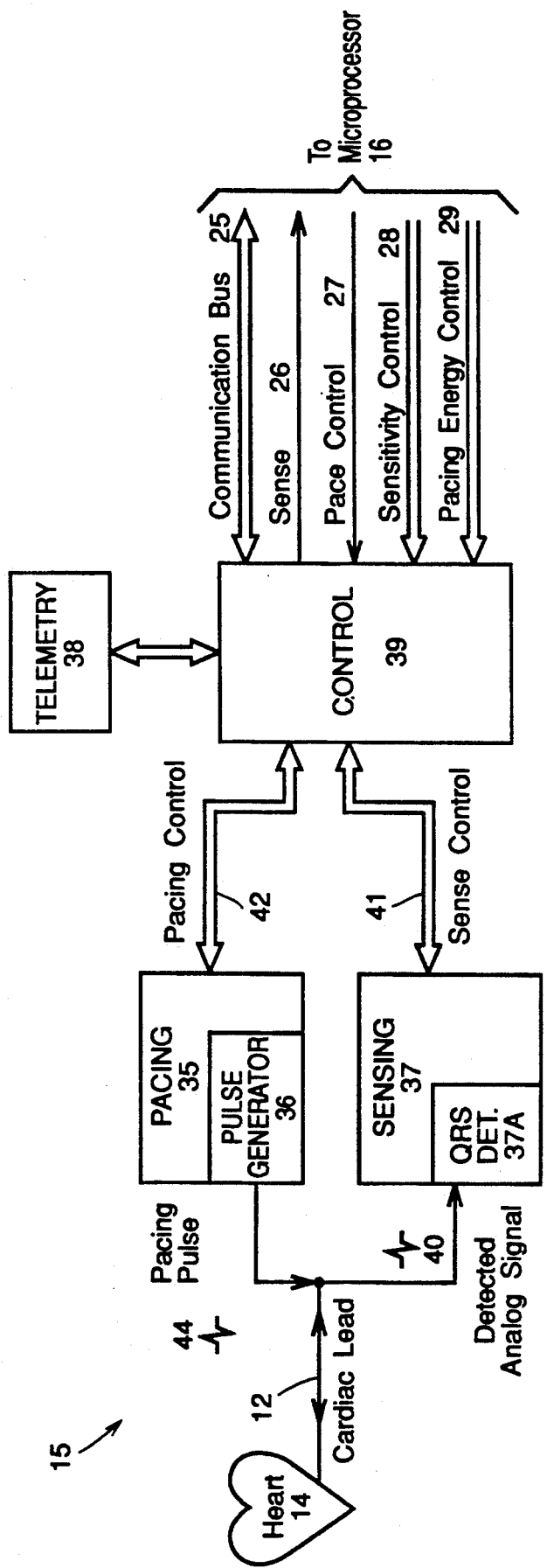
FIG. 2 depicts a block diagram of a pacemaker employed in the arrhythmia control systems of this invention.

Referring now to FIG. 2, pacemaker 15 comprises a pacing circuit 35 which includes a pacing pulse generator 36, a sensing circuit 37, and a telemetry circuit 38. In addition, there is a control block 39 which includes an interface to microprocessor 16.

In operation, sensing circuit 37 detects analog signals 40 from the heart 14 in an internal QRS detector 37A and converts the detected signals to digital signals. Furthermore, sensing circuit 37 receives an input sense control signal (which determines the sensitivity of the detection circuits in sensing circuit 37) by way of a sense control bus 41 from control block 39. As more fully described below, a change in this sensitivity will affect the voltage deviation required at the sensing electrode for a sense to be registered.

Pacing circuit 35 also receives inputs from control block 39 including a pace control and a pacing energy control by way of a pacing control bus 42 which carries the signals delivered by pace control line 27 and pacing energy control bus 29 from microprocessor 16. The pace control determines the type of pacing to occur while the magnitude of the pulse energy is determined by the pacing energy control. Pacing circuit 35 causes pulse generator 36 to generate a pacing pulse 44 which is delivered to the patient's heart 14 by means of cardiac lead system 12 which may either comprise a single lead or multiple leads.

Telemetry circuit 38 provides a bi-directional link between control block 39 of pacemaker 15 and an external device (not shown) such as a programmer. It allows data such as the operating parameters to be read from or altered in the implanted pulse module 11.

Figure 3:
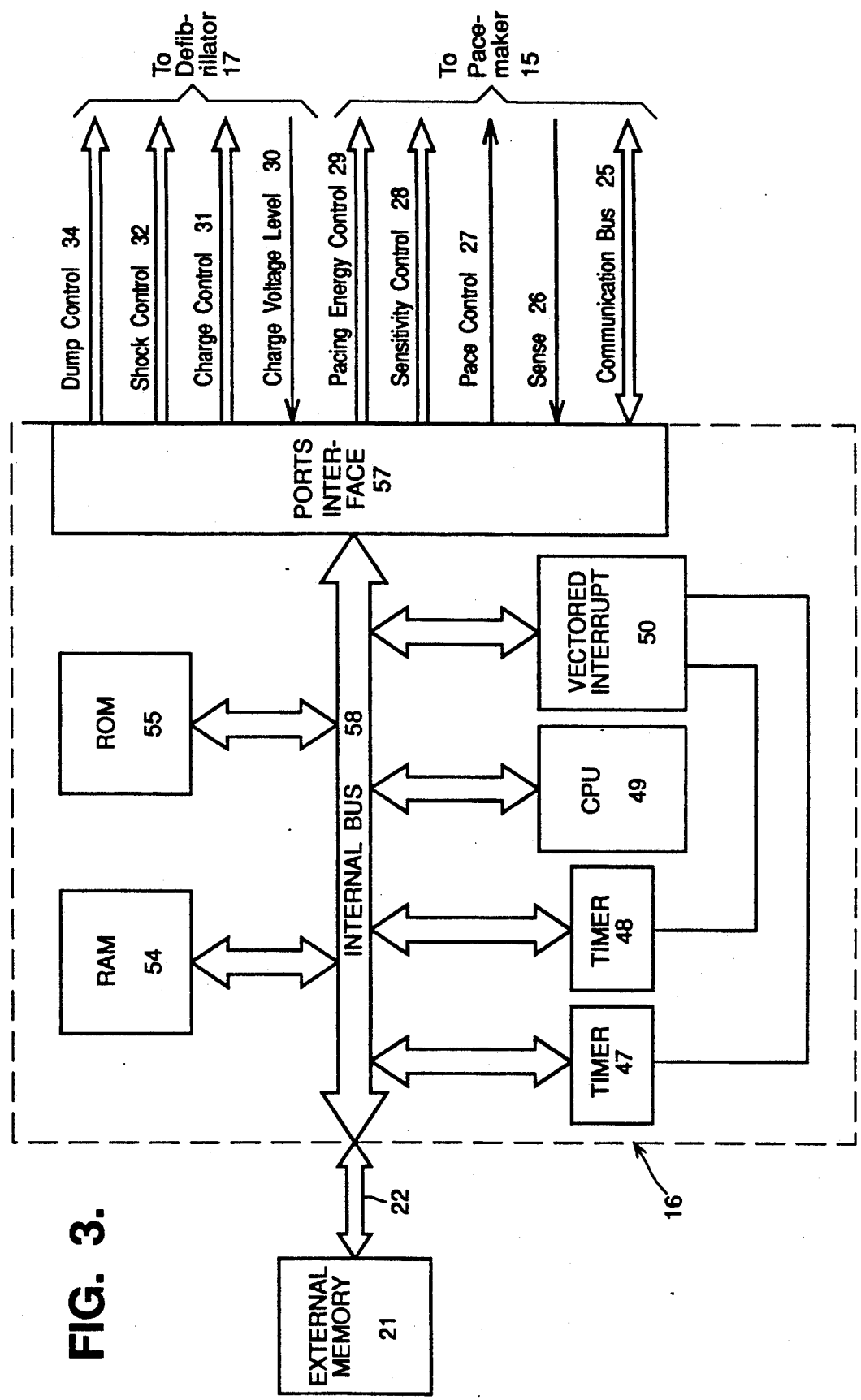
FIG. 3 depicts a block diagram of a microprocessor employed in the arrhythmia control systems of this invention.

Referring to FIG. 3, microprocessor 16 comprises two 16-bit timers 47 and 48, a CPU 49, a vectored interrupt block 50, a RAM 54, a ROM 55, a ports interface 57 and an internal communications bus 58. RAM 54 acts as a scratch pad and active memory during execution of the various programs stored in ROM 55 and used by microprocessor 16. These programs include system supervisory programs, detection algorithms for detecting various arrhythmias, as well as storage programs for storing, in external memory 21, data concerning the functioning of module 11 and the electrogram provided by cardiac lead 12. Timers 47 and 48 and associated control software implement some timing functions required by microprocessor 16 without resorting entirely to software, thus reducing computational loads on and power dissipation by CPU 49.

Signals received from telemetry circuit 38 (FIG. 2) permit an external programmer (not shown) to change the operating parameters of pacemaker 15 by supplying appropriate signals to control block 39 (FIG. 2). Communication bus 25 serves to provide signals indicative of such control to microprocessor 16. Thus, it is also possible for an external programmer to control operation of defibrillator 17 (FIG. 1A) by means of signals provided to microprocessor 16.

Appropriate telemetry commands may cause telemetry circuit 38 (FIG. 2) to transmit data to the external programmer. Data stored is read out, by microprocessor 16, on to communication bus 25, through control block 39 in pacemaker 15, and into the telemetry circuit 38 for transmission to the external programmer by a transmitter.

Microprocessor 16 receives various status and/or control inputs from pacemaker 15 and defibrillator 17. During normal pacer operations the input signal to pacemaker 15 is a sense signal on sense line 26 which is used by microprocessor 16 to perform operations such as arrhythmia detection. Microprocessor 16 produces outputs such as the pace control on pace control line 27 which determines the type of pacing to take place.

Other pacemaker control outputs generated by microprocessor 16 include a pacing energy control signal on pacing energy control bus 29 which determines the magnitude of the pulse energy, and a sensitivity control signal on sensitivity control bus 28, which determines the sensitivity setting of the sensing circuit.

Microprocessor 16 provides to defibrillator 17 a shock control signal on shock control bus 32 which indicates that a shock is to be delivered to the patient, a dump control signal on dump control bus 34 which indicates that a shock is to be dumped at an internal load within defibrillator 17, and a charge control signal on charge control bus 31 which determines the voltage level of the shock to be delivered. Charge voltage level line 30 provides a digital signal representative of charge voltage from an analog to digital converter within defibrillator 17, thus providing a feedback loop which assures that a shock of proper energy level is delivered by defibrillator 17.

With reference to FIG. 3, one technique of generating a train of micro-shocks for fibrillation induction is to time on timer 47 a delay period for a pre-programmed interval, triggered by a sense control on sense line 26, after which charge control bus 31 is activated and timer 48 is triggered. At the time-out of timer 48, charge control bus 31 is deactivated, shock control bus 32 is activated and timer 47 is triggered. For the delivery of a biphasic micro-shock for example, timer 47 would time out after the first phase of the micro-shock had been delivered to the defibrillator electrode leads 19A and 19B (FIG. 1A), and would trigger shock control line 32 to re-configure the shock control switches 106-109 shown in FIG. 4 (to be described in greater detail hereinafter) and would trigger timer 48 to deliver the second phase of the micro-shock. Numerous phases per micro-shock can be delivered by this technique. Following the micro-shock, timer 47 could then time-out a predetermined interval between micro-shocks while timer 48 controls the charge time. Thereafter, timer 47 would again control the duration of the first phase of the next micro-shock and timer 48 would control the duration of the second phase of this micro-shock. This micro-shock generation cycle could be repeated a number of times, as may be programmed in and controlled by CPU 49. CPU 49 also controls the configuration of each micro-shock in terms of polarity along shock control bus 32.

The time from the sense control trigger on sense line 26 to the beginning of the train, the charge time for each micro-shock, the width of each phase of each micro-shock, the interval between phases of each micro-shock, and the interval between successive micro-shocks can be individually controlled by timers 47 and 48. In another embodiment, a timer may be used to limit the length of the train of micro-shocks to a pre-determined duration.

Figure 4:
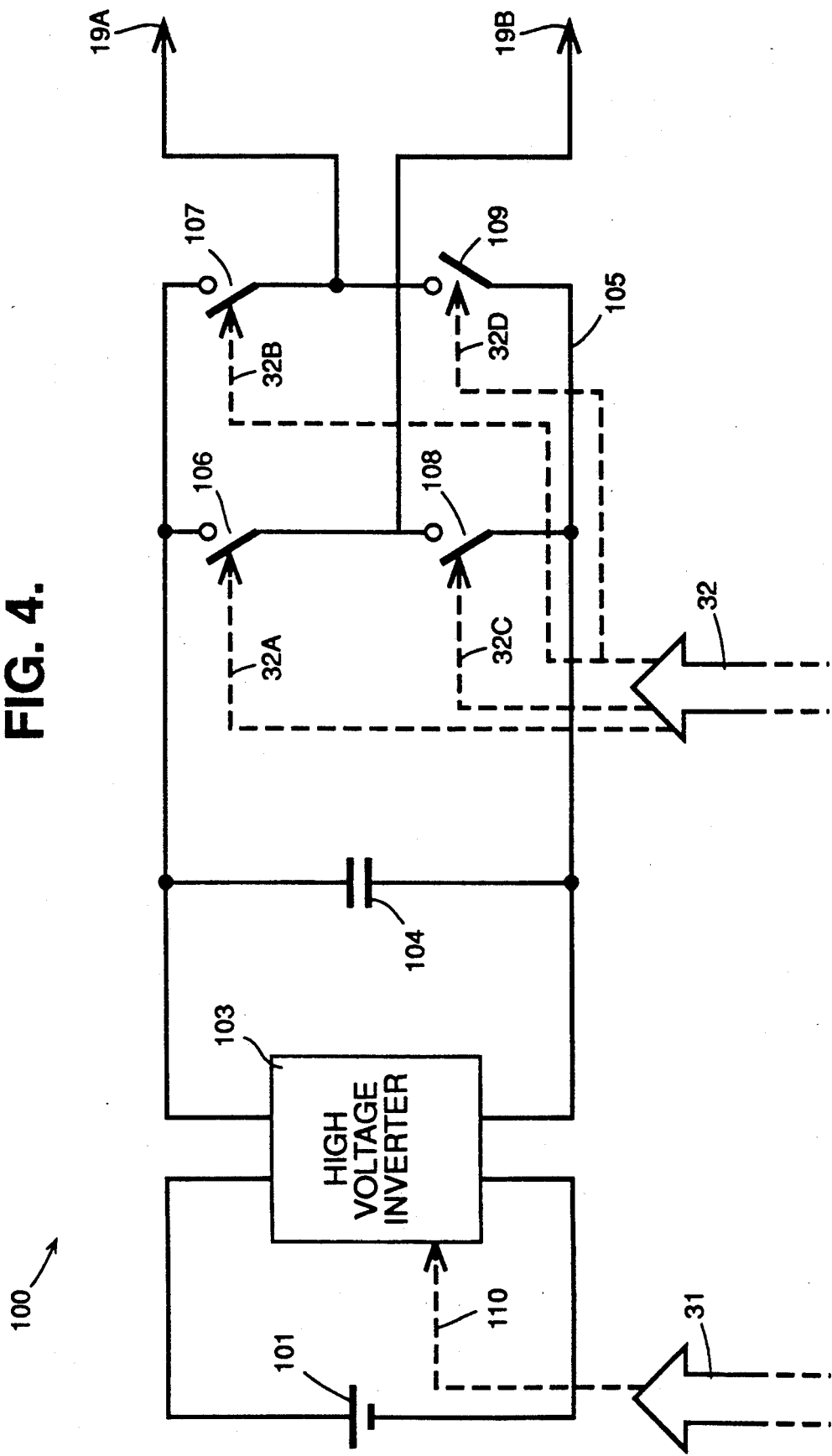
FIG. 4 shows a block diagram of a defibrillation and induction circuit employed in the arrhythmia control systems of this invention.

Referring now to FIG. 4, there is shown a block diagram of a defibrillation circuit, shown generally at 100, which is used in the invention for inducing fibrillation. Defibrillation circuit 100 includes a power supply or battery 101 which corresponds to the power supply 18 shown in FIGS. 1A and 1B. Battery 101 is connected to a high voltage inverter 103. A charge control signal 110 is received via charge control bus 31 and passes to the high voltage inverter 103. The charge control signal 110 is a programmed instruction which establishes the time during which a high voltage storage capacitor 104 is charged in order for it to acquire a certain voltage level. For example, if a micro-shock is required at a voltage of 7.5 V then the time to charge is 12 ms. On the other hand, if a voltage of 5 V is required for the micro-shock, then an 8 ms time for charging would be required. The charge control signal 110 is passed to the high voltage inverter 103 via the charge control bus 31. The high voltage storage capacitor 104 is responsive to the high voltage inverter 103 and charges to the appropriate energy level. For the purpose of the invention as described, the appropriate energy level is that energy level which is required for a micro-shock used in arrhythmia or fibrillation induction.

The defibrillation circuit 100 includes a high voltage output bridge switch, shown generally at 105, comprising four shock control switches 106, 107, 108, and 109. These four shock control switches receive shock control signals 32A, 32B, 32C, and 32D, respectively, which are relayed via the shock control bus 32. In this particular embodiment there are four shock control switches and four shock control signals to allow for micro-shocks or defibrillation shocks, which may be monophasic, biphasic or multiphasic. A multiphasic micro-shock or defibrillation shock is achieved by means of software programming techniques known to those skilled in the art, which provide appropriate control over the shock control switches. Additionally, and by similar well known programming means, these four shock control switches can control the polarity of a monophasic microshock and the polarity of the first phase of any multiphasic micro-shock. For arrhythmia or fibrillation induction, the micro-shocks may be delivered through the electrode lead system 19A and 19B, as in the case for defibrillation shocks, or through a combination of electrode lead system 12 (FIGS. 1A and 1B) and electrode lead system 19A and 19B, or through electrode lead system 12 alone.

Figure 5:
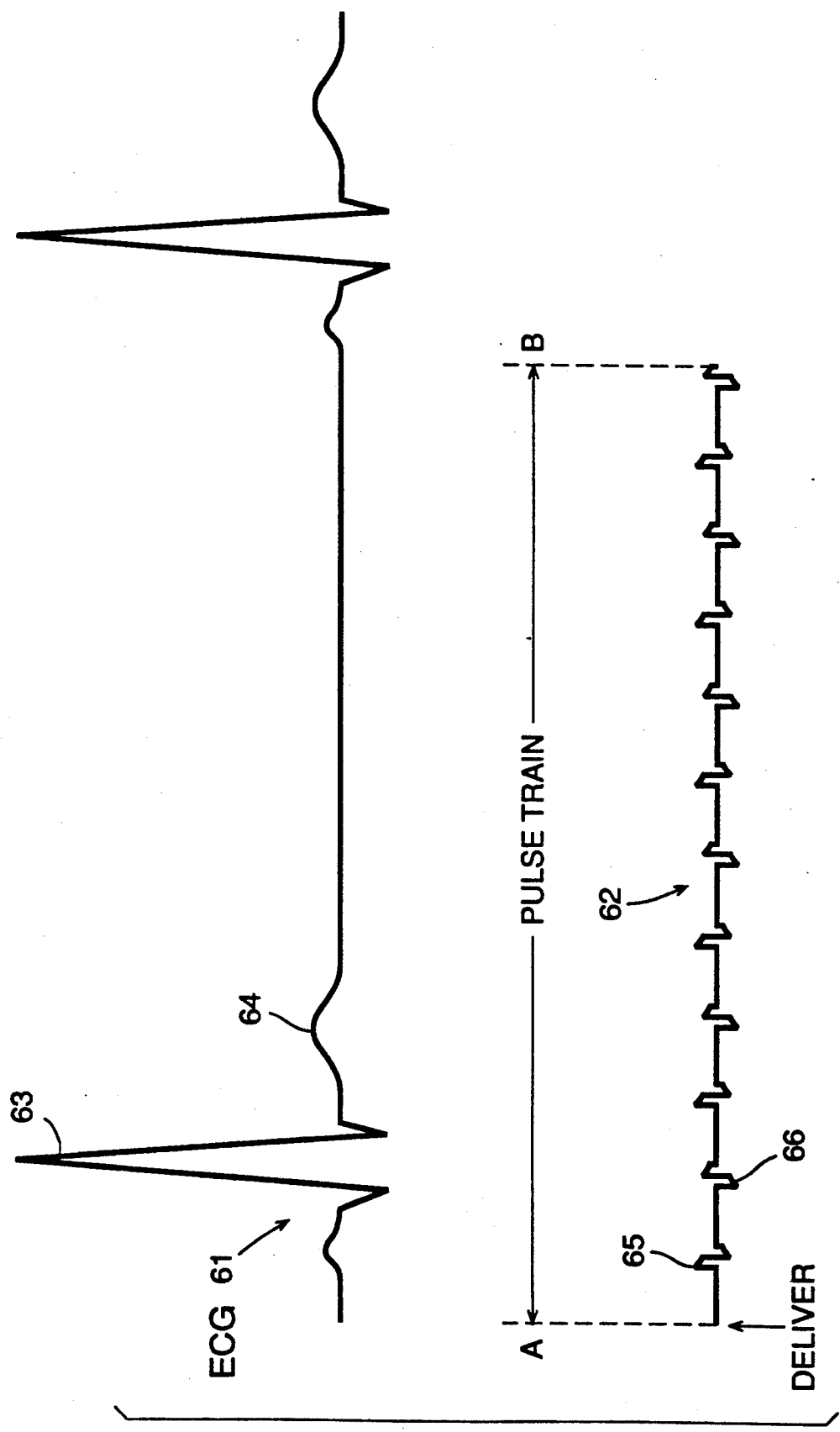
FIG. 5 depicts a patient's ECG and the waveform of fibrillation induction pulse train utilized in one embodiment of this invention; and, FIG. 6 depicts a patient's ECG and the waveform of fibrillation induction pulse trains utilized in another embodiment of this invention.

Referring to FIG. 5 there is depicted a patient's electrocardiogram or ECG, shown generally at 61, and the waveform of the fibrillation induction pulse train of microshocks, according to one embodiment of the invention, shown generally at 62. The patient's ECG 61 includes an R-wave 63 and a T-wave 64. The pulse train 62 includes micro-shocks 65 and 66 which are delivered in rapid succession by the defibrillation circuit 100 (FIG. 4) in order to induce a ventricular fibrillation in the patient's heart. The particular pulse train 61 shown in FIG. 5 is a continuous pulse train of micro-shocks delivered over a finite time duration defined by points A and B in FIG. 5. Micro-shock 65 and micro-shock 66, which comprise an adjacent pair of microshocks in pulse train 61, are reversed in polarity in this embodiment, as is the case for each adjacent pair of micro-shocks within the pulse train. Also, all of the micro-shocks in the pulse train shown in this embodiment are biphasic but could be programmed to be otherwise. The values and specifics of the micro-shock pulse width, amplitude, phase, the number of micro-shocks delivered, and other programmable parameters are provided through the software programming of the microprocessor 16. The details of software instructions are not shown as the programming methods are well known to those skilled in the art of biomedical engineering.

Figure 6:
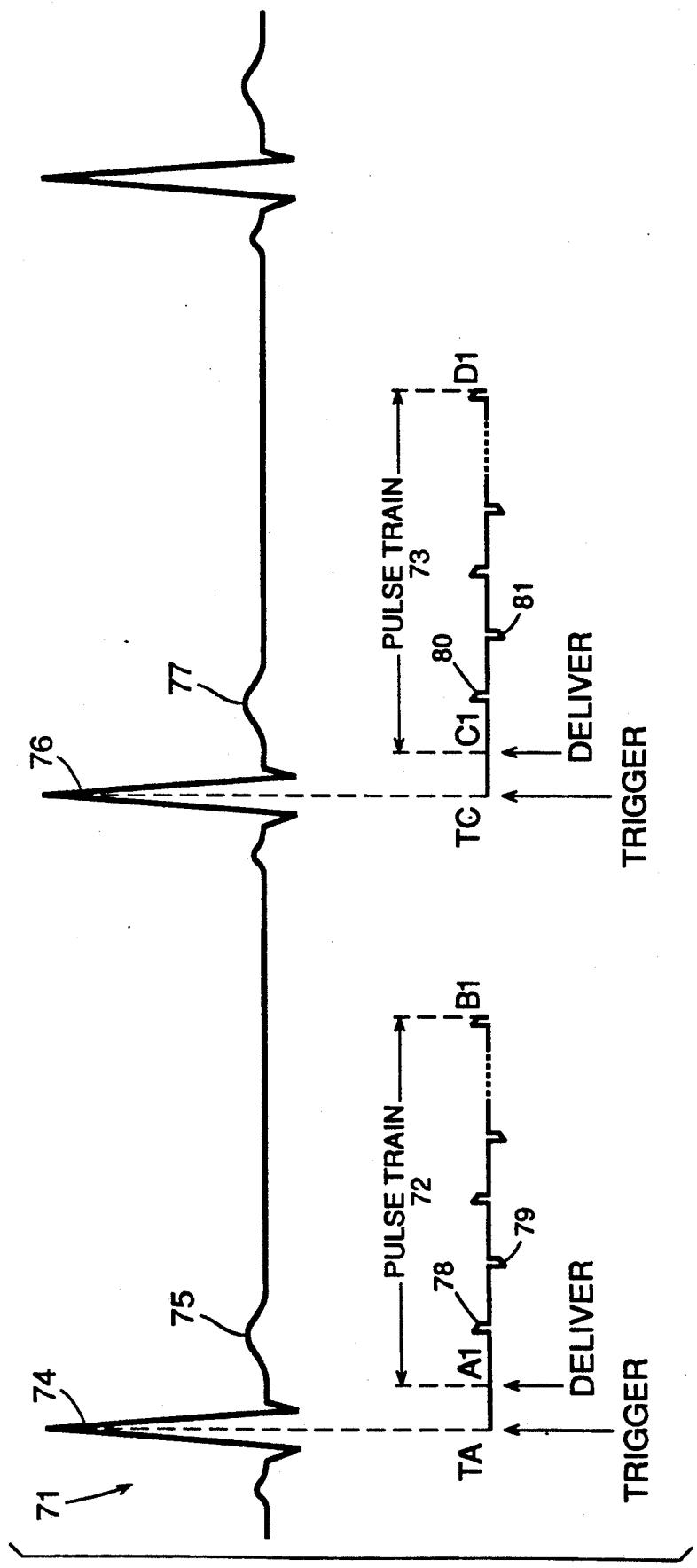

Referring to FIG. 6 there is depicted a patient's ECG, shown generally at 71, and the waveforms of the fibrillation induction pulse trains of micro-shocks, according to another embodiment of the invention, shown generally at 72 and 73. The patient's ECG 71 includes, R-waves at 74 and 76, and T-waves at 75 and 77. The method of fibrillation induction used in this embodiment, rather than being in the form of a continuous pulse train of micro-shocks, takes the form of a series of bursts of pulse trains, as shown at 72 and 73. Pulse train 72 is triggered at time TA by the detection of R-wave 74. There is then a post-triggering delay between time TA and the start of delivery of the pulse train at point A1. The delivery point A1 allows for the micro-shock 78 to coincide with the T-wave 75 for the purpose of achieving the most effective fibrillation induction. The pulse train 72 extends until termination point B1. Although the first micro-shock 78 coincides with the T-wave in the embodiment as shown, it is also possible in other embodiments that other micro-shocks which are not necessarily the first micro-shock in the train or sequence could coincide with the T-wave.

In an article by S. C. Hammill, entitled "Ventricular Arrhythmias", appearing at page 799 of Cardiology: Fundamentals and Practice, edited by R. O. Brandenburg, V. Fuster, E. R. Giuliani and D. C. McGoon, and published by Year Book Medical Publishers Inc., Chicago, U.S.A., 1987, it is stated, at p. 802, that in the cardiac cycle the middle third of the T-wave corresponds to the highest possible dispersion of refractoriness within the ventricles. As a result of this, the ventricles are most vulnerable to the initiation of arrhythmias during the middle third of the T-wave. Microshock 78 in the form of a trapezoidal wave is followed by microshock 79 which has a reverse polarity for the purpose of maintaining charge balancing. As in the case of the FIG. 5 embodiment, alternate micro-shocks are subjected to the same pattern of polarity reversal. Following timeout of the pulse train interval A1B1, there is a delay between time B1 and time TC. During this delay time, the circuitry awaits the sensing of the next R-wave 76. The sensing triggers the circuitry to commence the delivery of the next pulse train 73.

Following the post-triggering delay from TC to C1, the device commences pulse train 73 delivery with the first micro-shock 80 coinciding with the T-wave 77. Again, as with previous pulse train 72, the next microshock 81 is subjected to a polarity reversal and alternate micro-shocks have their polarity reversed, until timeout of the pulse train interval at D1.

Various aspects of the invention may be subject to programmability so that a physician may individualize the therapy for a particular patient's own needs. Also, by means of appropriate software programming, the device may automatically select from a combination of different parameters the most effective value of each parameter in order to achieve a competent arrhythmia induction. Furthermore, the invention may be automated to such an extent that the following parameters can be determined and set as a ratio of the cycle length of the patients cardiac rhythm or can be determined and set based on the amount of haemodynamic compromise that is extant: the interval between successive microshocks; the pulse widths of the microshocks; the pulse width of each phase of each microshock; the time delay between the phases of the micro-shocks; the delay between the trigger and the commencement of a train of micro-shocks; the delay between successive trains of micro-shocks; and, the duration of the train of micro-shocks. Equally, the invention may be automated such that the amplitude of the energy delivered for the induction of a fibrillation or other arrhythmia can be determined by increasing the voltage of the micro-shocks until capture of the cardiac cells is detected.

It is furthermore possible for the invention to pace the heart at a pre-programmed rate for a short period of time to entrain the heart muscle and cause it to contract at a steady and known rate, after which the device can deliver the arrhythmia induction train of micro-shocks using previously determined values for each of the programmable parameters.

As indicated above, one example of a programmable parameter is the micro-shock pulse energy, or amplitude, which is dependent on the amount of time during which the capacitors are charged. The pulse width of a micro-shock is another programmable feature.

The micro-shock frequency or repetition rate parameter may need to be adjustable in order to induce an arrhythmia at a required rate. This parameter may also be expressed as the inverse of the sum of the inter-micro-shock delay and the micro-shock pulse width. The delivery of continuous micro-shocks or the inclusion of discreet pulse trains is another available choice. If pulse trains are delivered by the device then there remains to be selected the number of trains, the number of micro-shocks in a train or the time duration of the train, and then the value of the time delay in between trains. Also, following triggering of a pulse train or a sequence of continuous micro-shocks, and prior to delivery of that pulse train or sequence of micro-shocks, there exists a programmable post-triggering delay period.

Furthermore, the actual feature of the patient's ECG or hemodynamic condition which triggers arrhythmia induction may be decided upon and programmed by a physician. For example, the triggering may be a result of R-wave sensing by means of an intracardiac electrogram which may be either endocardial or epicardial. The device may sense for the R-waves using either the sense-pace electrodes or the defibrillation electrodes. Alternately, triggering for the start of an arrhythmia induction may be initiated by a hemodynamic sensor such as the right ventricular peak systolic pressure, or other intra-cavitary pressure, intramural pressure, impedance changes, cardiac motion detectors, sonomicrometry, or a combination of these or other electrical, physiological, mechanical, or hemodynamic characteristics known to those skilled in pacemaker and defibrillator technology. The number of phases in the micro-shock may be subject to programmability with options of selecting monophasic, biphasic, triphasic or other multi-phasic microshocks. Also, the interval between successive phases may be a programmable option. Additionally, the choice of polarity reversal is available to allow for charge balancing, as are other modes of charge balancing such as the generation of a rising potential before and/or after the delivery of a micro-shock and being both opposite in polarity to the micro-shock and of equal amount of delivered charge.

Although the invention has been described with reference to a particular embodiment, it is to be understood that this embodiment is merely illustrative of the application of the principles of the invention. For example, the principle of the invention applies equally to single chamber defibrillator/pacemaker devices and dual chamber defibrillator/pacemaker devices which incorporate in their therapy both atrial and ventricular bradycardia and antitachycardia pacing, whereby the device has the capability of inducing fibrillation and other arrhythmias in both the atrium and the ventricle either separately or simultaneously. Examples of some other arrhythmias applicable to the invention are VT, SVT and AF. It may also be noted that the shape of the micro-shock waveforms are not necessarily limited to the trapezoidal waveform as described with reference to the drawings.

Further details on the shapes of waveforms attainable by the device are described in our co-pending U.S. application Ser. No. 780,757, filed Oct. 21, 1991; entitled "Apparatus and Method for the Generation of Varying Waveforms in an Arrhythmia Control System," which application is assigned to the same assignee as the present invention.

While there have been shown and described what are presently considered to be the preferred embodiments of this invention, it will be obvious to those skilled in the art that various other changes and modifications may be made without departing from the broader aspects of this invention. It is, therefore, aimed in the appended claims to cover all such changes and modifications as fall within the true spirit and scope of this invention.

What is claimed is:

1. An implantable medical device for providing therapy to a patient's inadequately functioning heart, comprising: means for detecting fibrillation; a defibrillation electrode lead system for delivering defibrillation therapy to the patient's heart; defibrillation circuit means for providing defibrillation therapy to said defibrillation electrode lead system, said defibrillation circuit means including means for storing an electrical charge, first control means coupled to said charge storing means for electrically charging said charge storing means to an appropriately high energy level for use in defibrillation therapy, in response to a detected tachycardia condition, and for electrically charging said charge storing means to an appropriately low energy level for selectively inducing arrhythmia in the patient's heart, and switching means for coupling said charge storing means to said defibrillation electrode lead system; said device further including second control means coupled to said switching means and operative when said first control means has electrically charged said charge storing means to a low energy level for selectively actuating said switching means to generate a plurality of micro-shocks from said low energy electrical charge in said charge storing means and to deliver said micro-shocks to said defibrillation electrode lead system for inducing said arrhythmia in the patient's heart.

2. An implantable medical device according to claim 1, further including timing means for controlling said micro-shocks, said timing means controlling intervals between said micro-shocks, pulse widths of said micro-shocks and duration of delivery of said micro-shocks.

3. An implantable medical device according to claim 1 further including means for pacing the heart wherein said device forms part of an implantable pacemaker/defibrillator device.

4. An implantable medical device according to claim 1, further including means for programming said device, and wherein the pulse energy of a said micro-shock is a programmable parameter.

5. An implantable medical device according to claim 1, further including means for programming said device, and wherein the pulse width of a said micro-shock is a programmable parameter.

6. An implantable medical device according to claim 1, further including means for programming said device, and wherein the number of phases of a said micro-shock is a programmable parameter.

7. An implantable medical device according to claim 6, further including means for reversing polarity of selected ones of said micro-shocks and selected phases of said micro-shocks.

8. An implantable medical device according to claim 1, further including means for programming said device, and wherein the pulse frequency of said micro-shocks is a programmable parameter.

9. An implantable medical device according to claim 1, further including means for programming said device, and wherein at least one of (a) the number of micro-shocks delivered and (b) the duration of delivery of said micro-shocks is a programmable parameter.

10. An implantable medical device according to claim 1, further including means for setting the interval between successive micro-shocks, the pulse widths of said micro-shocks, the pulse widths of each phase of each of said micro-shocks, the time delay between said phases of aid micro-shocks, and the duration of each train of micro-shocks based on at least one of (a) a ratio of the cycle length of the patient's cardiac rhythm and (b) the amount of haemodynamic compromise extant in the patient's heart.

11. An implantable medical device according to claim 1, further including means for increasing the voltage and the amplitude of the energy delivered for the induction of an arrhythmia until capture of the cardiac cells is detected.

12. An implantable medical device according to claim 1, further including a pacing electrode lead system, wherein at least a portion of the energy delivered in the form of said micro-shocks to the patient's heart is delivered by said pacing electrode lead system.

13. An implantable medical device according to claim 1, further including a pacing electrode lead system, wherein at least a portion of the number of said micro-shocks delivered to the patient's heart is delivered by said pacing electrode lead system.

14. An implantable medical device according to claim 1, further including means for reversing the polarity of at least a portion of the micro-shocks delivered during arrhythmia induction.

15. An implantable medical device according to claim 14, further including means for reversing polarity of each alternate individual micro-shock for the purpose of charge balancing.

16. An implantable medical device according to claim 1, further including means for delivering said micro-shocks in a series of one or more trains.

17. An implantable medical device according to claim 16, further including means for delivering a short run of pacing pulses to entrain the contractions of the heart prior to delivery of said micro-shocks to the patient's heart so that the delivery of said train of micro-shocks can be synchronized relative to the patient's cardiac cycle.

18. An implantable medical device according to claim 16, further including means for programming said device, means for triggering said micro-shock train, means for providing a post-triggering delay period prior to delivery of a said train, and wherein said post-triggering delay period is a programmable parameter.

19. An implantable medical device according to claim 18, further including means for setting the interval between successive micro-shocks, the pulse widths of said micro-shocks, the pulse widths of each phase of each said micro-shock, the time delay between said phases of said micro-shocks, the delay between the trigger and the commencement of a train of microshocks, the delay between successive trains of micro-shocks, and the duration of each train of micro-shocks based on at least one of (a) a ratio of the cycle length of the patient's cardiac rhythm and (b) the amount of haemodynamic comprise extant in the patient's heart.

20. An implantable medical device according to claim 16, further including means responsive to a sensing of the patient's R-wave for triggering the start of delivery of said series of trains.

21. An implantable medical device according to anyone of claims 16 or 20, further including means for synchronizing the delivery of at least a portion of a said train of micro-shocks to the patient's T-wave.

22. An implantable medical device according to any one of claims 16 or 20, further including means for programming said device, and wherein the length of the said series of trains and the widths of said micro-shock pulses are programmable parameters which may be programmed by a physician to suit a patient's individual need.

23. An implantable medical device according to any one of claims 16 or 20, further including means for programming said device, and wherein the number of said trains, the number of micro-shocks in a train, and the time delay between successive trains are programmable parameters.

24. A method for inducing fibrillation in and providing defibrillation therapy to a patient's inadequately functioning heart, comprising the steps of:
providing an implantable medical device including a fibrillation detection means, a defibrillation electrode lead system for delivering defibrillation therapy to the patient's heart and a defibrillation circuit having an electrical charge storing mans therein for providing defibrillation therapy to the defibrillation electrode lead system;
charging said charge storing means to an appropriately high energy level for use in defibrillation therapy in response to a detected tachycardia condition, and to an appropriately low energy level for inducing arrhythmia in the patient's heart at selected other times;
generating a plurality of micro-shocks from energy derived from said charge storing means; and,
delivering at least a portion of said micro-shocks to the patient's heart through said defibrillation electrode lead system to induce said arrhythmia therein.

25. A method according to claim 24, wherein said device includes a timing means for controlling said micro-shocks, and said method includes the further steps of controlling the intervals between, the pulse widths of, and the duration of delivery of said micro-shocks.

26. A method according to claim 24, wherein said device is programmable and includes at least one of the following programmable parameters: the pulse energy of a said micro-shock, the pulse width of a said micro-shock, the number of phases of a said micro-shock, the pulse frequency of said micro-shocks, the number of said micro-shocks, delivered, and the duration of delivery of said micro-shocks; and wherein said method includes the further step of programming at least one of said programmable parameters.

27. A method according to claim 26, wherein said programming step includes the sub-step of basing the programming setting of said at least one programmable parameter on at least one of (a) a ratio of the cycle length of the patient's cardiac rhythm and (b) the amount of haemodynamic compromise extant in the patient's heart.

28. A method according to claim 24, including, in the event that capture of cardiac cells is not detected upon delivery of said appropriately low energy level, the further step of increasing the voltage amplitude of the energy delivered for the induction of an arrhythmia until capture of the cardiac cells is detected.

29. A method according to claim 24, wherein said device further includes a pacing electrode lead system, and wherein said micro-shock delivering step includes the substep of delivering at least a portion of the energy of said micro-shocks to the patient's heart through said pacing electrode lead system.

30. A method according to claim 24, including the further step of reversing the polarity of at least a portion of the micro-shocks delivered during arrhythmia induction.

31. A method according to claim 30, wherein said polarity reversing step includes the sub-step of reversing the polarity of each alternate individual micro-shock for the purpose of charge balancing.

32. A method according to claim 30, wherein said polarity reversing step includes the sub-step of reversing the polarity of selected portions of individual ones of said micro-shocks.

33. A method according to claim 24, wherein the step of generating said micro-shocks includes the sub-step of generating said micro-shocks in a series of one or more trains, and wherein the step of delivering said micro-shocks includes the sub-step of delivering said micro-shocks in said series of one of more trains.

34. A method according to claim 33, wherein said device forms part of a pacemaker/defibrillator, and wherein said method includes the further step of delivering a short run of pacing pulses to entrain contractions of the heart prior to delivery of said micro-shocks so that the delivery of said train of micro-shocks can be synchronized relative to the patient's cardiac cycle.

35. A method according to claim 33, further including the step of triggering the start of delivery of said series of trains in response to a sensing of the patient's R-wave.

36. A method according to any one of claims 33 or 35, including the further step of synchronizing the delivery of at least a portion of a said train of micro-shocks to the patient's T-wave.

37. A method according to claim 35, including the further step of providing a post-trigger delay period following said triggering step so that a said micro-shock is delivered in synchrony with the patient's T-wave.

* * * * *